(12) United States Patent
Rabe et al.

(10) Patent No.: US 7,173,079 B2
(45) Date of Patent: Feb. 6, 2007

(54) CASTING MATERIAL FOR PRODUCING CASTING MOLDS FOR CASTING HIGH-MELTING POINT MATERIALS

(75) Inventors: Susanne Rabe, Darmstadt (DE);
Wolfgang Eiselt, Darmstadt (DE);
Reinhard Lenk, Dresden (DE);
Hans-Jürgen Richter, Dresden (DE)

(73) Assignees: Schutz-Dental GmbH, Rosbach (DE);
Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 0 days.

(21) Appl. No.: 10/496,359

(22) PCT Filed: Dec. 7, 2001

(86) PCT No.: PCT/IB01/02358

§ 371 (c)(1),
(2), (4) Date: Dec. 20, 2004

(87) PCT Pub. No.: WO03/047790

PCT Pub. Date: Jun. 12, 2003

(65) Prior Publication Data

US 2005/0103228 A1    May 19, 2005

(51) Int. Cl.
*C08K 3/18* (2006.01)
*C08K 3/22* (2006.01)
*B28B 7/34* (2006.01)
*B22C 1/22* (2006.01)
*B22C 9/02* (2006.01)

(52) U.S. Cl. .................. 524/321; 524/430; 524/433; 106/38.9; 164/35; 164/529

(58) Field of Classification Search ............... 524/321, 524/430, 433; 164/35, 529; 106/38.9
See application file for complete search history.

(56) References Cited

U.S. PATENT DOCUMENTS 4,097,935 A * 7/1978 Jarcho ................. 623/23.61
4,207,306 A * 6/1980 Jarcho ................. 423/633

* cited by examiner

*Primary Examiner*—Kriellion Sanders
(74) *Attorney, Agent, or Firm*—Rankin, Hill, Porter & Clark LLP

(57) ABSTRACT

The casting-mold material designed to manufacture casting molds used in casting high melting-point substances. The casting mold formed from a powder component containing magnesium oxide and aluminum oxide and a liquid component. The powder component additionally contains a calcium aluminate and an alkali fluoride or an earth alkali fluoride and the liquid component contains a polyelectrolyte and a basic component, the latter determining the liquid component pH value between 10 and 14. A fluid slip is prepared by mixing the powder and liquid components and is dried, hardened and sintered to produce a hollow mold.

37 Claims, No Drawings

CASTING MATERIAL FOR PRODUCING CASTING MOLDS FOR CASTING HIGH-MELTING POINT MATERIALS

The present invention relates to a casting-mold material used to manufacture casting molds for casting high-melting point substances as defined in the preamble of claim 1.

This casting-mold material is composed of a powder component and of a liquid component which are stirred into a fluid slip that, following drying and hardening, shall be manufactured by sintering into a hollow mold. The ceramic mold so made is filled With a molten metal, preferably molten titanium or titanium alloys. Upon removing the mold, the cast objects will offer good details.

The casting mold material is appropriate for casting titanium and titanium alloys, in particular for dental applications to produce precisely fitted dental crowns, bridges or model casts offering excellent surface qualities and free of gas inclusions. Because the molten substance will shrink after being poured into the casting mold and then will solidify, the ceramic hollow mold must be made to expand commensurately following sintering. This compensation is implemented by one or several expansible components in the casting mold material.

When being cooled, titanium and titanium alloys shrink substantially less then a conventional dental alloys such as of gold/cobalt or chromium/cobalt. As regards the known encapsulating substances being used, compensation of expansion is carried out by adding ammonium dihydrogen phosphate, which reacts with magnesium oxide to form coarse $MgNH_4PO_4 \times 6H_2O$ and by changing the phase of silicon dioxide. Advantageously quartzes and phosphates shall not be used because they react with the titanium melt.

The objective of the present invention is to create a casting-mold material which is more fluid, more universally applicable and less time consuming and more economical than the casting-mold materials of the known state of the art.

The invention attains the above objective using a casting-mold material exhibiting the features of claim 1.

The casting-mold material of the present invention attains expansion by forming spinel above approximately 850° C. in the preheat oven. Compared to the state of the art, the casting-mold material exhibits far better fluidity, higher green hardness and more rapid setting. It also offers the advantage of being suitable not only for casting dental crowns and bridges, but also as a universal, encapsulating substance for speed and model casting.

The improved fluidity of the casting-mold material of the present invention is mainly attained by means of the polyelectrolyte. The higher green mechanical strength and hence the feasibility of model casting is attained by the calcium aluminate. The setting rate is determined in part by the calcium aluminate and by the ingredients of the liquid component. The zirconium oxide implements the improved resistance to thermal shocks.

In a preferred embodiment mode of the present invention, the powder component of the casting-mold material additionally contains spinel, appropriately in a proportion by weight of 0.1 to 20.0%, preferably 1 to 10%. The spinel admixture allows controlling the expansion. Appropriately the spinel exhibits a median grain size $d_{50}$ of 3 to 20 microns, preferably 8 to 12 microns.

Appropriately the powder component contains by weight 40 to 60%, preferably 45 to 55% magnesium oxide, also 15 to 30%, preferably 21 to 29% aluminum oxide. Moreover the powder component may appropriately contain by weight 0.5 to 20.0%, preferably 1 to 10% zirconium oxide. Increased mechanical strength is attained thereby following sintering, furthermore increased hardness and higher thermal resistance.

Appropriately the calcium aluminate in the powder component should be present in proportions by weight of 5 to 30%, preferably 10 to 20%. This proportion assures improved green mechanical strength and improved control of material setting.

Lastly the powder component may appropriately contain lithium fluoride in a proportion by weight of 0.5 to 20.0%, preferably 1 to 10%, to attain higher green mechanical strength.

The polyelectrolyte contained in the liquid component may be a polycarboxylic acid, preferably a polyacrylic acid or a polymethacrylic acid or one of their salts. Said polyelectrolyte appropriately should be present in a proportion by weight of 0.2 to 10.0%, preferably 0.5–3.0%.

Moreover the liquid component appropriately should contain a basic component, preferably an alkali hydroxide (for instance lithium hydroxide) in a proportion by weight of 0.5 to 10.0%, preferably 1 to 9%.

A preferred embodiment mode of the present invention makes use of magnesium oxide in coarse and fine form, said coarse form exhibiting a median grain size $d_{50}$ of 100 to 170 microns, preferably 110 to 140 microns and the fine form exhibiting a median grain size $d_{50}$ less than 10 microns, preferably 3 to 7 microns. The fine magnesium oxide causes accelerated setting and the coarse magnesium oxide causes improved resistance to thermal shock.

The weight ratio of coarse to fine magnesium oxide appropriately shall be between 9:1 and 5:1, preferably 8:1 to 6:1.

The median grain size $d_{50}$ of the aluminum oxide used in the powder component of the present invention shall be between 3 and 15 microns, preferably between 5 and 10 microns.

The zirconium oxide used preferentially in the powder component appropriately shall exhibit a median grain size $d_{50}$ between 3 and 15 microns, preferably between 5 and 10 microns.

The calcium aluminate used in the powder component appropriately shall exhibit a median grain size $d_{50}$ of 5 to 20 microns, preferably a median grain size $d_{50}$ between 8 and 12 microns.

Appropriately the liquid component is water, preferably de-ionized or distilled water, optionally containing an added alcohol having a boiling point less than 100° C., preferably ethanol, 1-propanol, 2-propanol or tertiary butyl alcohol. Because the alcohol evaporates more easily than water, better drying is attained.

The invention and its further developments are elucidated below by several illustrative embodiment modes.

EMBODIMENT MODE 1

| Powder component (all data in % by wt) | | Liquid component (all data in % by wt) | |
|---|---|---|---|
| Magnesium oxide | 51.5 | Lithium hydroxide | 2.0 |
| Aluminum oxide | 25.0 | Polyacrylic acid sodium salt | 2.0 |
| Zirconium oxide | 4.0 | Water | 96.0 |
| Calcium aluminate | 14.5 | | 100.0 |
| Lithium fluoride | 7.0 | | |
| Spinel | 1.0 | | |
| | 100.0 | | |

The mixing rate is 100 g powder component to 18 ml liquid component. Mixing time is 60 seconds. Setting time is 45 minutes.

EMBODIMENT MODE 2

| Powder component (all data in % by wt) | | Liquid component (all data in % by wt) | |
|---|---|---|---|
| Magnesium oxide | 55.5 | Lithium hydroxide | 1.0 |
| Aluminum oxide | 21.0 | Polyacrylic acid sodium salt | 0.7 |
| Zirconium oxide | 3.0 | Isopropanol | 4.0 |
| Calcium aluminate | 13.0 | Water | 94.3 |
| Lithium fluoride | 5.5 | | 100.0 |
| Spinel | 2.0 | | |
| | 100.0 | | |

The mixing rate is 200 g powder component to 37 ml liquid component. Mixing time is 45 seconds and setting time is 40 minutes.

EMBODIMENT MODE 3

| Powder component (all data in % by wt) | | Liquid component (all data in % by wt) | |
|---|---|---|---|
| Magnesium oxide | 52.0 | Lithium hydroxide | 1.0 |
| Aluminum oxide | 23.0 | Polymethacrylic acid | 1.5 |
| Zirconium oxide | 6.0 | Isopropanol | 3.0 |
| Calcium aluminate | 11.5 | Water | 94.5 |
| Lithium fluoride | 7.0 | | 100.0 |
| Spinel | 0.5 | | |
| | 100.0 | | |

The mixing rate is 200 g powder component to 37 ml liquid component. Mixing time is 45 seconds and setting time is 40 minutes.

EMBODIMENT MODE 4

| Powder component (all data in % by wt) | | Liquid component (all data in % by wt) | |
|---|---|---|---|
| Magnesium oxide | 50.0 | Lithium hydroxide | 1.0 |
| Aluminum oxide | 25.0 | Polyacrylic acid Na salt | 3.0 |
| Zirconium oxide | 5.0 | Water | 96.0 |
| Calcium aluminate | 12.0 | | 100.0 |
| Lithium fluoride | 4.0 | | |
| Spinel | 4.0 | | |
| | 100.0 | | |

The mixing rate is 200 g powder component to 37 ml liquid component. Mixing time is 60 seconds and setting time is 40 minutes.

To manufacture the casting-mold material of the present invention, the powder component and the liquid component are mixed or kneaded together in the manner of one of the above Embodiment Modes 1 through 4. The liquid component contains a polyelectrolyte assuming that in the first place the casting-mold material shall be adequately fluid. Accordingly stirring provides a fluid, castable mass which shall be poured around the master model of the cast body, said master model consisting of wax or a plastic burning without leaving a residue. Solidification of the liquid mass in part takes place by the calcium aluminate setting hydraulically. The setting rate of the liquid mass may be adjusted by the quantity of calcium aluminate and magnesium oxide as well as by the composition of the liquid component in such manner that said mass may be processed conveniently while a very short setting time may still be attained.

Following being poured into a warm and vibration-free space, the mixed mass is allowed to set for at least 45 minutes. After about 45 minutes, the mass that has set can be placed into an appropriate preheating oven and the oven program sintering the encapsulating substance may be started. This stage requires about 6 h, and during that time waxes, plastics and water will be expelled, the spinel expansion then ensuing.

Illustratively the oven program comprises a heating stage at a temperature rate of 4° K/minute until a temperature of 300° C. has been reached, further a 30-minute dwell time at 300° C., another heating stage at the rate of 7° K/minute until reaching a temperature of 900° C. and a cooling stage down to 450° C. Thereupon the sintered hollow mold is filled with molten titanium at a casting temperature of 450° C. in a vacuum pressurized casting mold under an inert gas.

The invention claimed is:

1. A casting-mold material to manufacture casting molds for casting high melting-point substances, said material comprising:
   (A) a powder component comprising magnesium oxide and aluminum oxide, and
   (B) a liquid component, wherein
   (C) the powder component further comprises a calcium aluminate and an alkali fluoride or an earth alkali fluoride, and
   (D) the liquid component comprises a polyelectrolyte and a basic component, said basic component determining the pH value of the liquid component between 10 and 14.

2. The casting-mold material as claimed in claim 1, wherein the powder component further comprises zirconium oxide.

3. The casting-mold material as claimed in claim 1, wherein the basic component includes an alkali hydroxide.

4. The casting-mold material as claimed in claim 1, wherein the powder component further comprises spinel.

5. The casting-mold material as claimed in claim 1, wherein the alkali fluoride is selected from the group consisting of lithium fluoride and sodium fluoride.

6. The casting-mold material as claimed in claim 1, wherein the basic component determines the pH value between 11 and 13.

7. The casting-mold material as claimed in claim 2, wherein the powder component contains a proportion by weight of zirconium oxide of 0.5 to 20%.

8. The casting-mold material as claimed in claim 1, wherein the powder component contains a proportion by weight of calcium aluminate of 5.0 to 30.0%.

9. The casting-mold material as claimed in claim 1, wherein the powder component contains a proportion by weight of one of alkali fluoride and earth alkali fluoride of 0.5 to 20%.

10. The casting-mold material as claimed in claim 1, wherein the powder component contains a proportion by weight of spinel of 0.1 to 20.0%.

11. The casting-mold material as claimed in claim 1, wherein the liquid component contains a proportion by weight of a polyelectrolyte of 0.2 to 10.0%.

12. The casting-mold material as claimed in claim 1, wherein the liquid component contains a proportion by weight of the basic component, which is an alkali hydroxide, of 0.5 to 10.0%.

13. The casting-mold material as claimed in claim 1, wherein the polyelectrolyte contains a polycarboxylic acid.

14. The casting-mold material as claimed in claim 1, wherein the magnesium oxide is present in coarse form and in fine form, a median grain size $d_{50}$ of the coarse form being 100 to 170 microns, and the median grain size $d_{50}$ of the fine form being less than 10 microns.

15. The casting-mold material as claimed in claim 14, wherein the magnesium oxide is present in a ratio by weight of coarse form to fine form of 9:1 to 5:1.

16. The casting-mold material as claimed in claim 1, wherein the aluminum oxide exhibits a median grain size $d_{50}$ of 3 to 15 microns.

17. The casting-mold material as claimed in claim 2, wherein a median grain size $d_{50}$ of the zirconium oxide is 3 to 15 microns, preferably 5 to 10 microns.

18. The casting-mold material as claimed in claim 1, wherein a median grain size d50 of the calcium aluminate is 5 to 20 microns.

19. The casting-mold material as claimed in claim 1, wherein a median grain size $d_{50}$ of the spinel is 3 to 20 microns.

20. The casting-mold material as claimed in claim 1, wherein the liquid component contains water, said water being selected from the group consisting of de-ionized water and distilled water.

21. The casting-mold material as claimed in claim 1, wherein the liquid component comprises an alcohol having a boiling point lower than 100° C., said alcohol being selected from the group consisting of ethanol, 1-propanol, 2-propanol, and tertiary butyl alcohol.

22. A fluid slip, prepared by mixing the powder component with the liquid component of the casting-mold material claimed in claim 1.

23. A method for casting titanium and titanium alloys comprising the steps of:
   providing a casting mold manufactured from a casting mold material comprising:
   (A) a powder component comprising magnesium oxide and aluminum oxide, and
   (B) a liguid component, wherein
   (C) the powder component further comprises a calcium aluminate and an alkali fluoride or an earth alkali fluoride, and
   (D) the liguid component comprises a polyelectrolyte and a basic component, said basic component determining the pH value of the liguid comnonent between 10 and 14; and
   pouring molten titanium or titanium alloy into said casting mold.

24. The casting-mold material as claimed in claim 1, wherein the basic component includes lithium hydroxide.

25. The casting-mold material as claimed in claim 2, wherein the powder component contains a proportion by weight of zirconium oxide of 1 to 10%.

26. The casting-mold material as claimed in claim 1, wherein the powder component contains a proportion by weight of calcium aluminate of 20.0 to 20.0%.

27. The casting-mold material as claimed in claim 1, wherein the powder component contains a proportion by weight of one of alkali fluoride and earth alkali fluoride of 1 to 10%.

28. The casting-mold material as claimed in claim 1, wherein the powder component contains a proportion by weight of spinel of 1 to 10.0%.

29. The casting-mold material as claimed in claim 1, wherein the liquid component contains a proportion by weight a polyelectrolyte of 0.5 to 3.0%.

30. The casting-mold material as claimed in claim 1, wherein the liquid component contains a proportion by weight of the basic component, which is an alkali hydroxide, of 1 to 9%.

31. The casting-mold material as claimed in claim 13, wherein the polycarboxylic acid is selected from the group consisting of polyacrylic acid, polymethacrylic acid, and one of their salts.

32. The casting-mold material as claimed in claim 1, wherein the magnesium oxide is present in coarse form and in fine form, a median grain size $d_{50}$ of the coarse form being 100 to 140 microns, and the median grain size $d_{50}$ of the fine form being between about 3 to 7 microns.

33. The casting-mold material as claimed in claim 32, wherein the magnesium oxide is present in a ratio by weight of coarse form to fine form of 8:1 to 6:1.

34. The casting-mold material as claimed in claim 1, wherein the aluminum oxide exhibits a median grain size $d_{50}$ of 5 to 10 microns.

35. The casting-mold material as claimed in claim 2, wherein a median grain size $d_{50}$ of the zirconium oxide is 5 to 10 microns.

36. The casting-mold material as claimed in claim 1, wherein a median grain size $d_{50}$ of the calcium aluminate 8 to 12 microns.

37. The casting-mold material as claimed in claim 1, wherein a median grain size $d_{50}$ of the spinel 8 to 12 microns.

* * * * *

UNITED STATES PATENT AND TRADEMARK OFFICE
CERTIFICATE OF CORRECTION

PATENT NO. : 7,173,079 B2 Page 1 of 1
APPLICATION NO. : 10/496359
DATED : February 6, 2007
INVENTOR(S) : Rabe et al.

It is certified that error appears in the above-identified patent and that said Letters Patent is hereby corrected as shown below:

Column 6, Line 1 (Claim 23, Line 11), delete "liguid" and insert --liquid--.

Column 6, Line 3 (Claim 23, Line 13), delete "liguid comnonent" and insert --liquid component--.

Signed and Sealed this

Third Day of April, 2007

JON W. DUDAS
*Director of the United States Patent and Trademark Office*